US011255862B2

(12) United States Patent
Henrotin et al.

(10) Patent No.: US 11,255,862 B2
(45) Date of Patent: Feb. 22, 2022

(54) OSTEOMODULIN AND OSTEOMODULIN FRAGMENTS AS BIOMARKERS FOR OSTEOARTHRITIS AND USE THEREOF

(71) Applicant: Université de Liège, Liège (BE)

(72) Inventors: Yves Henrotin, Boncelles (BE); Christelle Sanchez, Fraipont (BE); Edwin De Pauw, Marchin (BE); Gabriel Mazzucchelli, Liège (BE)

(73) Assignee: UNIVERSITÉ DE LIÈGE, Liège (BE)

( * ) Notice: Subject to any disclaimer, the term of this patent is extended or adjusted under 35 U.S.C. 154(b) by 581 days.

(21) Appl. No.: 16/140,851

(22) Filed: Sep. 25, 2018

(65) Prior Publication Data
US 2019/0011459 A1 Jan. 10, 2019

Related U.S. Application Data

(63) Continuation-in-part of application No. PCT/EP2016/080348, filed on Dec. 8, 2016.

(30) Foreign Application Priority Data

Mar. 25, 2016 (EP) .................................... 16162499

(51) Int. Cl.
G01N 33/68 (2006.01)
C07K 16/28 (2006.01)
(52) U.S. Cl.
CPC ......... G01N 33/6893 (2013.01); C07K 16/28 (2013.01); G01N 33/6887 (2013.01);
(Continued)
(58) Field of Classification Search
None
See application file for complete search history.

(56) References Cited

U.S. PATENT DOCUMENTS

2003/0004311 A1* 1/2003 Baker .............. G01N 33/57484
530/350
2011/0189694 A1* 8/2011 Woloszczuk ....... G01N 33/6887
435/7.1

FOREIGN PATENT DOCUMENTS

WO 2010/046443 A2 4/2010

OTHER PUBLICATIONS

International Search Report, dated Mar. 6, 2017 (4 pages).
(Continued)

Primary Examiner — Rebecca M Giere
(74) Attorney, Agent, or Firm — Jacob Holman PLLC

(57) ABSTRACT

The present invention refers to osteomodulin (OMD) protein or fragment of osteomodulin (OMD) protein for use in the prognosis and/or diagnosis of osteoarthritis and/or subchondral bone sclerosis of mammals, preferably human individuals. The present invention further refers to a method for prognosis and/or diagnosis of osteoarthritis and/or subchondral bone sclerosis, comprising the following steps: i) measuring osteomodulin (OMD) protein or a fragment or fragments of osteomodulin (OMD) protein in samples of body fluids of mammalian individuals, preferably human serum samples; ii) judging that decreased levels of osteomodulin (OMD) protein or of said fragment(s) compared to levels in body fluids, preferably serum, of healthy individuals indicate onset of osteoarthritis and/or subchondral bone sclerosis. The present invention also provides an immunological binding partner specifically binding to osteomodulin (OMD) protein or fragment of osteomodulin (OMD) protein for use in the prognosis and/or diagnosis of osteoarthritis and/or subchondral bone sclerosis of mammals, preferably human individuals and a kit comprising said immunological binding partner.

5 Claims, 6 Drawing Sheets

Specification includes a Sequence Listing.

(52) U.S. Cl.
CPC ...... *C07K 2317/34* (2013.01); *G01N 2333/51* (2013.01); *G01N 2333/78* (2013.01); *G01N 2800/105* (2013.01); *G01N 2800/52* (2013.01)

(56) References Cited

OTHER PUBLICATIONS

Crowther, "Enzyme-linked Immunosorbent Assay (ELISA)", Molecular Biomethods Handbook, Rapley et al., Humana Press Inc, Totowa 1998, pp. 657-682.

Harlow and Lane eds, Antibodies: A Laboratory Manual, Cold Spring Haror Laboratory Press 1988, Chapter 3: Antibody-Antigen interactions, pp. 23-35.

Ausubel et al., Current Protocols in Molecular Biology, John Wiley & Sons, Inc. New York 199, Ch. 11, Table 11.2.1 Summary of ELISA Protocols.

Ninomiya et al., "Osteoclastic activity induces osteomodulin expression in osteoblasts", Biochemical and Biophysical Research Communication, Academic Press Inc., vol. 362, No. 2, Sep. 10, 2007, pp. 460-466, cited in the ISR.

Bay-Jensen et al., "Osteoarthitis year in review 2015: soluble biomarkers and the BIPED criteria", Osteoarthritis and Cartilage, vol. 24, No. 1, Jan. 31, 2016, pp. 9-20, cited in the ISR.

Sanchez-Sabate et al., "Identification of differentially expressed genes in trabecular bone from the iliac crest of osteoarthritic patients", Osteoarthritis and Cartilage, vol. 17, No. 8, Aug. 1, 2009, pp. 1106-1114, cited in the ISR.

Henrotin et al., "Soluble biomarkers development in osteoarthritis: from discovery to personalized medicine", Biomarkers, vol. 20, No. 8, Nov. 17, 2015, pp. 540-546, cited in the ISR.

Hunter et al., "Biomarkers for osteoarthritis: Current position and steps towards further validation", Bailliere's Best Practice and Research Clinical Rheumatology, vol. 28, No. 1, Feb. 1, 2014, pp. 61-71, cited in the ISR.

Henrotin et al., "Osteoarthritis biomarkers derived from cartilage extracellular matrix: Current status and future perspectives", Annals of Physical and Rehabilitation Medicine, Apr. 1, 2016, pp. 1-4, cited in the ISR.

\* cited by examiner

SEQUENCE LISTING

```
<160> NUMBER OF SEQ ID NOS: 9

<210> SEQ ID NO 1
<211> LENGTH: 421
<212> TYPE: PRT
<213> ORGANISM: Homo sapiens
<220> FEATURE:
<223> OTHER INFORMATION: Osteomodulin

<400> SEQUENCE: 1

Met Gly Phe Leu Ser Pro Ile Tyr Val Ile Phe Phe Phe Gly Val
1               5                   10                  15

Lys Val His Cys Gln Tyr Glu Thr Tyr Gln Trp Asp Glu Asp Tyr Asp
                20                  25                  30

Gln Glu Pro Asp Asp Asp Tyr Gln Thr Gly Phe Pro Phe Arg Gln Asn
            35                  40                  45

Val Asp Tyr Gly Val Pro Phe His Gln Tyr Thr Leu Gly Cys Val Ser
        50                  55                  60

Glu Cys Phe Cys Pro Thr Asn Phe Pro Ser Ser Met Tyr Cys Asp Asn
65                  70                  75                  80

Arg Lys Leu Lys Thr Ile Pro Asn Ile Pro Met His Ile Gln Gln Leu
                85                  90                  95

Tyr Leu Gln Phe Asn Glu Ile Glu Ala Val Thr Ala Asn Ser Phe Ile
            100                 105                 110

Asn Ala Thr His Leu Lys Glu Ile Asn Leu Ser His Asn Lys Ile Lys
        115                 120                 125
```

-continued

Ser Gln Lys Ile Asp Tyr Gly Val Phe Ala Lys Leu Pro Asn Leu Leu
    130                 135                 140

Gln Leu His Leu Glu His Asn Asn Leu Glu Glu Phe Pro Phe Pro Leu
145                 150                 155                 160

Pro Lys Ser Leu Glu Arg Leu Leu Leu Gly Tyr Asn Glu Ile Ser Lys
                165                 170                 175

Leu Gln Thr Asn Ala Met Asp Gly Leu Val Asn Leu Thr Met Leu Asp
            180                 185                 190

Leu Cys Tyr Asn Tyr Leu His Asp Ser Leu Leu Lys Asp Lys Ile Phe
        195                 200                 205

Ala Lys Met Glu Lys Leu Met Gln Leu Asn Leu Cys Ser Asn Arg Leu
210                 215                 220

Glu Ser Met Pro Pro Gly Leu Pro Ser Ser Leu Met Tyr Leu Ser Leu
225                 230                 235                 240

Glu Asn Asn Ser Ile Ser Ser Ile Pro Glu Lys Tyr Phe Asp Lys Leu
                245                 250                 255

Pro Lys Leu His Thr Leu Arg Met Ser His Asn Lys Leu Gln Asp Ile
            260                 265                 270

Pro Tyr Asn Ile Phe Asn Leu Pro Asn Ile Val Glu Leu Ser Val Gly
        275                 280                 285

His Asn Lys Leu Lys Gln Ala Phe Tyr Ile Pro Arg Asn Leu Glu His
290                 295                 300

Leu Tyr Leu Gln Asn Asn Glu Ile Glu Lys Met Asn Leu Thr Val Met
305                 310                 315                 320

Cys Pro Ser Ile Asp Pro Leu His Tyr His His Leu Thr Tyr Ile Arg
                325                 330                 335

Val Asp Gln Asn Lys Leu Lys Glu Pro Ile Ser Ser Tyr Ile Phe Phe
            340                 345                 350

Cys Phe Pro His Ile His Thr Ile Tyr Tyr Gly Glu Gln Arg Ser Thr
        355                 360                 365

Asn Gly Gln Thr Ile Gln Leu Lys Thr Gln Val Phe Arg Arg Phe Pro
370                 375                 380

Asp Asp Asp Asp Glu Ser Glu Asp His Asp Asp Pro Asp Asn Ala His
385                 390                 395                 400

Glu Ser Pro Glu Gln Glu Gly Ala Gly His Phe Asp Leu His Tyr
                405                 410                 415

Tyr Glu Asn Gln Glu
            420

<210> SEQ ID NO 2
<211> LENGTH: 93
<212> TYPE: PRT
<213> ORGANISM: Homo sapiens
<220> FEATURE:
<223> OTHER INFORMATION: synthetic peptide

<400> SEQUENCE: 2

Lys Ile Asp Tyr Gly Val Phe Ala Lys Leu Pro Asn Leu Leu Gln Leu
1               5                   10                  15

His Leu Glu His Asn Asn Leu Glu Glu Phe Pro Phe Pro Leu Pro Lys
            20                  25                  30

Ser Leu Glu Arg Leu Leu Leu Gly Tyr Asn Glu Ile Ser Lys Leu Gln
        35                  40                  45

Thr Asn Ala Met Asp Gly Leu Val Asn Leu Thr Met Leu Asp Leu Cys
    50                  55                  60

```
Tyr Asn Tyr Leu His Asp Ser Leu Leu Lys Asp Lys Ile Phe Ala Lys
 65                  70                  75                  80

Met Glu Lys Leu Met Gln Leu Asn Leu Cys Ser Asn Arg
                 85                  90
```

<210> SEQ ID NO 3
<211> LENGTH: 61
<212> TYPE: PRT
<213> ORGANISM: Homo sapiens
<220> FEATURE:
<223> OTHER INFORMATION: synthetic peptide

<400> SEQUENCE: 3

```
Met Tyr Leu Ser Leu Glu Asn Asn Ser Ile Ser Ile Pro Glu Lys
 1               5                  10                  15

Tyr Phe Asp Lys Leu Pro Lys Leu His Thr Leu Arg Met Ser His Asn
                 20                  25                  30

Lys Leu Gln Asp Ile Pro Tyr Asn Ile Phe Asn Leu Pro Asn Ile Val
             35                  40                  45

Glu Leu Ser Val Gly His Asn Lys Leu Lys Gln Ala Phe
     50                  55                  60
```

<210> SEQ ID NO 4
<211> LENGTH: 15
<212> TYPE: PRT
<213> ORGANISM: Homo sapiens
<220> FEATURE:
<223> OTHER INFORMATION: synthetic peptide

<400> SEQUENCE: 4

```
Leu Glu His Asn Asn Leu Glu Glu Phe Pro Phe Pro Leu Pro Lys
 1               5                  10                  15
```

<210> SEQ ID NO 5
<211> LENGTH: 15
<212> TYPE: PRT
<213> ORGANISM: Homo sapiens
<220> FEATURE:
<223> OTHER INFORMATION: synthetic peptide

<400> SEQUENCE: 5

```
Leu Arg Met Ser His Asn Lys Leu Gln Asp Ile Pro Tyr Asn Ile
 1               5                  10                  15
```

<210> SEQ ID NO 6
<211> LENGTH: 21
<212> TYPE: DNA
<213> ORGANISM: Homo sapiens
<220> FEATURE:
<223> OTHER INFORMATION: primer

<400> SEQUENCE: 6
tgtaatgacc agtcaacagg g                                           21

<210> SEQ ID NO 7
<211> LENGTH: 18
<212> TYPE: DNA
<213> ORGANISM: Homo sapiens
<220> FEATURE:
<223> OTHER INFORMATION: primer

<400> SEQUENCE: 7
tgcctgacca aggaaagc                                               18

```
<210> SEQ ID NO 8
<211> LENGTH: 22
<212> TYPE: DNA
<213> ORGANISM: Homo sapiens
<220> FEATURE:
<223> OTHER INFORMATION: primer

<400> SEQUENCE: 8
tcctggtttg ccttcttcac tt                                              22

<210> SEQ ID NO 9
<211> LENGTH: 23
<212> TYPE: DNA
<213> ORGANISM: Homo sapiens
<220> FEATURE:
<223> OTHER INFORMATION: primer

<400> SEQUENCE: 9
gggtcaatag aaggacacat cac                                             23
```

OSTEOMODULIN AND OSTEOMODULIN FRAGMENTS AS BIOMARKERS FOR OSTEOARTHRITIS AND USE THEREOF

This is a Continuation-in-part application of PCT/EP2016/080348 filed Dec. 8, 2016 in English, claiming the priority of European Application EP 16162499.4, filed Mar. 25, 2016, all of which are hereby incorporated by reference.

The present invention refers to a method for diagnosis or determining prognosis of osteoarthritis and/or subchondral bone sclerosis and osteomodulin and fragments thereof as biomarkers for osteoarthritis and use thereof.

Osteoarthritis (OA) is the most common joint disease and is a major cause of joint pain and disability in the aging population. Its etiology is multifactorial (i.e., age, obesity, joint injury. genetic predisposition), and the pathophysiologic process affects the entirety of the joint. Destruction of articular cartilage, sclerosis of subchondral bone, and formation of osteophytes, synovial inflammation, and ligament and meniscal damage constitute the main features characterizing OA.

Besides finding management strategies for OA, the challenge is also to identify tools that could help the prognosis, the diagnosis and monitoring of disease progression and assess the efficacy of new therapeutic interventions. These tools need to be accurate and sensitive enough to identify early event at the molecular level and objectively assess the efficacy of novel or pre-existing therapeutic modalities. Soluble biomarkers are likely to be among these tools.

So far, only cartilage-derived biomarkers are used in osteoarthritis. Mainly used are fragments coming from Type II collagen (Coll2-1. Coll2-1 NO2. C2C, PIINP, CTXII), aggrecan (MMPs or ADAMTSs generated neoepitopes, Keratan sulfate or CS846), COMP or Fibulin-3.

Furthermore, currently no single specific marker is able to prognose and/or diagnose precisely the pathology. Therefore, at present a combination of different markers reflecting different aspects of the pathology has to be used. Indeed, OA is a heterogeneous syndrome with different clinical phenotypes defined by risk factors, progression profiles. co-morbidities, signs and symptoms. In current diagnostic methods for in osteoarthritis only cartilage-derived biomarkers are used.

Therefore, the technical object of the present invention was to provide a new marker, a single specific marker and a method for prognosing and diagnosing precisely the pathology of osteoarthritis.

SUMMARY OF THE PRESENT INVENTION

When pursuing the studies of the present invention the present inventors discovered that osteomodulin is less expressed and less secreted by sclerotic subchondral osteoblasts during osteoarthritis (OA). Further, the present inventors found fragments of osteomodulin in body fluids, in particular in serum, of OA patients, and that serum concentrations of the osteomodulin fragments were lower than compared to those of healthy individuals.

Therefore, the present invention provides the following (1) to (14):

(1) Osteomodulin (OMD) protein or fragment of osteomodulin (OMD) protein for use in the prognosis and/or diagnosis of osteoarthritis and/or subchondral bone sclerosis of mammals. preferably human individuals.

(2) Osteomodulin (OMD) protein or fragment of osteomodulin (OMD) protein for use according to (1), wherein decreased expression or decreased concentration in body fluids of said osteomodulin protein or its fragment(s) compared to healthy individuals indicate onset of osteoarthritis and/or subchondral bone sclerosis.

(3) Osteomodulin (OMD) protein or fragment of osteomodulin (OMD) protein for use according to (2), wherein said decreased expression or decreased concentration is measured in body fluids selected from the group consisting of urine, secretions, interstitial fluid, blood, synovial fluid, serum, spinal fluid lymph, preferably serum. Decreased body fluid levels, in particular decreased serum levels, of said
osteomodulin (OMD) protein or said fragment(s) compared to healthy individuals indicate onset of osteoarthritis and/or subchondral bone sclerosis.

(4) Osteomodulin (OMD) protein or fragment of osteomodulin (OMD) protein for use according to any one of (1) to (3), wherein full-length osteomodulin protein is having the amino acid sequence shown in SEQ ID NO: 1, wherein osteomodulin (OMD) protein is a protein represented by the amino acid positions 1-421 or by the amino acid positions 21-421 of SEQ ID NO: 1; and wherein said fragment is selected from the group consisting a) to f):

a) osteomodulin fragment having N-terminal amino acid residue varying from amino acid position 21 to 148 and having C-terminal amino acid residue varying from amino acid position 162 to 235 in the amino acid sequence shown in SEQ ID NO: 1; b) osteomodulin fragment having N-terminal amino acid residue varying from amino acid position 224 to 261 and having C-terminal amino acid residue varying from amino acid position 276 to 421 in the amino acid sequence shown in SEQ ID NO: 1;

c) OMD-(131-223).
d) OMD-(236-296),
e) OMD-(148-162),
f) OMD-(261-276).

(5a) Preferred Osteomodulin fragments are osteomodulin fragment having N-terminal amino acid residue varying from amino acid position 131 to 148 and having C-terminal amino acid residue varying from amino acid position 162 to 223 in the amino acid sequence shown in SEQ ID NO: 1;

Or (b) osteomodulin fragment having N-terminal amino acid residue varying from amino acid position 236 to 261 and having C-terminal amino acid residue varying from amino acid position 276 to 296 in the amino acid sequence shown in SEQ ID NO: 1;

(6) Osteomodulin (OMD) protein or fragment of osteomodulin protein for use according to any one of (1) to (5). wherein the fragment according to (4) a), c) and e) or (5) a) is specifically bound by an immunological binding partner raised against OMD-(148-162).

(7) Osteomodulin (OMD) protein or fragment of osteomodulin protein for use according to any one of (1) to (5). wherein the fragment according to (4) b), d) and f) or (5) a) is specifically bound by an immunological binding partner raised against OMD-(261-276).

(8) Method for prognosis and/or diagnosis of osteoarthritis and/or subchondral bone sclerosis. comprising the following steps:

i) measuring osteomoduhn (OMD) protein or a fragment or fragments of osteomoduhn (OMD) protein in samples of body fluids of mammalian individuals, preferably human serum samples;

ii) judging that decreased levels of osteomoduhn (OMD) protein or of said fragment(s) compared to levels in body fluids, preferably serum, of healthy individuals indicate onset of osteoarthritis and/or subchondral bone sclerosis.

(9). Method for determining or checking or diagnosis of the therapeutic effect of treatment of osteoarthritis and/or subchondral bone sclerosis in a mammalian individual, preferably a human individual, comprising the following steps:

i) measuring osteomoduhn (OMD) protein or a fragment or fragments of osteomoduhn (OMD) protein in samples of body fluids, preferably serum samples, of said individual during or after treatment;

ii) judging that either one of (1) to (3)

(1) normal levels of osteomoduhn (OMD) protein or of said fragment(s) in the samples obtained in step i), or (2) increased levels of osteomoduhn (OMD) protein or of said fragment(s) in said samples obtained in step i) compared to levels in samples of body fluids, preferably serum samples, of said individual before said treatment. or (3) increased levels of osteomoduhn (OMD) protein or of said fragment(s) in said samples obtained in step i) compared to levels in samples of body fluids, preferably serum samples, of healthy individuals, indicate a therapeutic effect of the treatment of osteoarthritis and/or subchondral bone sclerosis in said individual.

(10) The method according to (8) or (9), wherein full-length osteomoduhn protein is having the amino acid sequence shown in SEQ ID NO: 1, wherein osteomoduhn (OMD) protein to be measured in step i) is a protein represented by the amino acid positions 1-421 or by the amino acid positions 21-421 of SEQ ID NO: 1; and wherein said fragment to be measured in step i) is selected from the group consisting a) to f):

a) osteomodulin fragment having N-terminal amino acid residue varying from amino acid position 21 to 148 and having C-terminal amino acid residue varying from amino acid position 162 to 235 in the amino acid sequence shown in SEQ ID NO: 1; b) osteomodulin fragment having N-terminal amino acid residue varying from amino acid position 224 to 261 and having C-terminal amino acid residue varying from amino acid position 276 to 421 in the amino acid sequence shown in SEQ ID NO: 1;

c) OMD-(131-223),
d) OMD-(236-296),
e) OMD-(148-162).
f) OMD-(261-276).

(11) Preferred fragments to be measured in step i) are:

a) osteomodulin fragment having N-terminal amino acid residue varying from amino acid position 131 to 148 and having C-terminal amino acid residue varying from amino acid position 162 to 223 in the amino acid sequence shown in SEQ ID NO: 1: or b) osteomodulin fragment having N-terminal amino acid residue varying from amino acid position 236 to 261 and having C-terminal amino acid residue varying from amino acid position 276 to 296 in the amino acid sequence shown in SEQ ID NO: 1:

In preferred methods according to any one of (8) to (11), for measuring the body fluid levels, preferably serum levels, in step i) an immunological binding partner is used which is selected from the group consisting of polyclonal antibodies, monoclonal antibodies, humanized antibodies, Fc fragments, Fab fragments, single chain antibodies (scFv), chimeric antibodies, biobetters and other antigen-specific antibody fragments.

(12) The method according to (10) or (11), wherein the fragment according to (10) a), c) and c) or (11) a), is specifically bound by an immunological binding partner raised against OMD-(148-162);

and/or wherein the fragment according to (10) b), d) and f) or (11) b). is specifically bound by an immunological binding partner raised against OMD-(261-276).

(13) The method according to (10) or (11), wherein at least two osteomodulin fragment species are measured, namely any one of (10) a), c) and e), or (11) a), and any one of (10) b), d) and f) or (11) b).

(14) Fragment of osteomodulin protein, wherein full-length osteomodulin protein is having the amino acid sequence shown in SEQ ID NO: 1. and wherein said fragment is selected from the group consisting a) to f):

a) osteomodulin fragment having N-terminal amino acid residue varying from amino acid position 21 to 148 and having C-terminal amino acid residue varying from amino acid position 162 to 235 in the amino acid sequence shown in SEQ ID NO: 1: b) osteomodulin fragment having N-terminal amino acid residue varying from amino acid position 224 to 261 and having C-terminal amino acid residue varying from amino acid position 276 to 421 in the amino acid sequence shown in SEQ ID NO: 1;

c) OMD-(131-223).
d) OMD-(236-296),
e) OMD-(148-162),
f) OMD-(261-276).

(15) Preferred fragments are:

a) osteomodulin fragment having N-terminal amino acid residue varying from amino acid position 131 to 148 and having C-terminal amino acid residue varying from amino acid position 162 to 223 in the amino acid sequence shown in SEQ ID NO: 1: b) osteomodulin fragment having N-terminal amino acid residue varying from amino acid position 236 to 261 and having C-terminal amino acid residue varying from amino acid position 276 to 296 in the amino acid sequence shown in SEQ ID NO: 1;

(16) Immunological binding partner specifically binding to osteomodulin (OMD) protein or fragment of osteomodulin (OMD) protein for use in the prognosis and/or diagnosis of osteoarthritis and/or subchondral bone sclerosis of mammals, preferably human individuals.

(17) Immunological binding partner specifically binding to an osteomodulin fragment, wherein full-length osteomodulin protein is having the amino acid sequence shown in SEQ ID NO: 1 I and wherein said fragment is selected from the group consisting a) to f):

a) osteomodulin fragment having N-terminal amino acid residue varying from amino acid position 21 to 148 and having C-terminal amino acid residue varying from amino acid position 162 to 235 in the amino acid sequence shown in SEQ ID NO: 1; b) osteomodulin fragment having N-terminal amino acid residue varying from amino acid position 224 to 261 and having C-terminal amino acid residue varying from amino acid position 276 to 421 in the amino acid sequence shown in SEQ ID NO: 1;

c) OMD-(131-223),
d) OMD-(236-296),
e) OMD-(148-162),
f) OMD-(261-276).

(18) Immunological binding partner specifically binding to preferred fragments that are:

osteomodulin fragment having N-terminal amino acid residue varying from amino acid position 131 to 148 and having C-terminal amino acid residue varying from amino acid position 162 to 223 in the amino acid sequence shown in SEQ ID NO: 1; or osteomodulin fragment having N-terminal amino acid residue varying from amino acid position 236 to 261 and having C-terminal amino acid residue varying from amino acid position 276 to 296 in the amino acid sequence shown in SEQ ID NO: 1;

In preferred embodiments of the immunological binding partner according to (17) or (18) the immunological binding partner is selected from the group consisting of polyclonal antibodies, monoclonal antibodies, humanized antibodies. Fc fragments, Fab fragments, single chain antibodies (scFv), chimeric antibodies, biobetters and other antigen-specific antibody fragments.

(19) Kit comprising the immunological binding partner according to anyone of claim 16 or 18, wherein said immunological binding partner preferably is selected from the group consisting of polyclonal antibodies, monoclonal antibodies, humanized antibodies. Fc fragments. Fab fragments, single chain antibodies (scFv), chimeric antibodies, biobetters and other antigen-specific antibody fragments.

The present invention provides osteomodulin and fragments thereof as a single specific marker that is able to determine prognose and/or to diagnose precisely the pathology of OA. In particular the present invention provides osteomodulin (OMD) protein or fragment of osteomodulin protein for use in the prognosis and/or diagnosis of osteoarthritis and/or subchondral bone sclerosis of mammals, preferably human individuals. In particular. a method is provided for prognosis and/or diagnosis of osteoarthritis and/or subchondral bone sclerosis, using osteomodulin (OMD) protein or fragment(s) of osteomodulin protein as a marker for the prognosis and/or diagnosis of osteoarthritis and/or subchondral bone sclerosis of mammals, preferably human individuals. In particular, the osteomodulin (OMD) protein or fragment of osteomodulin (OMD) protein are used in said prognosis and/or diagnosis in that way that decreased expression or decreased concentration in body fluids of said osteomodulin protein or its fragment(s) compared to healthy individuals indicate onset of osteoarthritis and/or subchondral bone sclerosis. In a further preferred embodiments decreased expression or decreased concentration is measured in body fluids selected from the group consisting of urine, secretions, interstitial fluid, blood, synovial fluid, serum, spinal fluid lymph, more preferably serum.

The method according to the present invention comprises i) measuring osteomodulin (OMD) protein or a fragment or fragments of osteomodulin (OMD) protein in samples of body fluids of mammalian individuals, preferably human serum samples; ii) judging that decreased levels of osteomodulin (OMD) protein or of said fragment(s) compared to body fluids levels, preferably serum levels, of healthy individuals indicate onset of osteoarthritis and/or subchondral bone sclerosis.

Osteomodulin is an extracellular matrix keratan sulfate proteoglycan member of the small leucine-rich repeat protein family. For some time osteomodulin was thought to be bone specific but recently osteomodulin expression was also observed in other articular tissues like articular chondrocytes and labrum-derived fibrochondrocytes. Little is known about the biological activity of osteomodulin. It may be implicated in biomineralization processes and has a function in binding of osteoblasts via the alpha(V) beta(3)-integrin. Osteomodulin is able in vitro to stimulate aggrecan expression by articular chondrocytes. The mature form of osteomodulin of *Homo sapiens* is represented by the amino acid sequence 21-421 of SEQ ID NO: 1. The amino acid sequence shown in SEQ ID NO: 1 of the sequence listing of this application also includes amino acid positions 1 to 20. The mature form of the protein has a molecular weight of 49.5 kDa but depending to the glycosylation pattern it's estimated around 60 to 85 kDa. The COOH terminal peptide binds to the bone hydroxyapatite.

During the studies for the present invention the present inventors identified by using proteomic techniques osteomodulin and fragments thereof as new possible soluble biomarkers coming from the secretome of primary subchondral osteoblasts. The present inventors found that osteomodulin is less expressed and less secreted by sclerotic subchondral osteoblasts during OA. Moreover, fragments of osteomodulin were found in human serum. Serum concentrations of the osteomodulin fragments were found to be significantly lower than those of healthy individuals.

The data and in vitro results obtained suggest that osteomodulin can be considered to represent a potential biomarker of osteoarthritis, or of a subset of osteoarthritis patients with subchondral bone changes. Quantifying osteomodulin or osteomodulin fragment level in serum indicates a particular state of the disease and can be used in diagnosis and prognosis of osteoarthritis and or other ageing-related diseases, and also in monitoring the efficacy of treatment for osteoarthritis and/or ageing-related diseases.

The method of the present invention for prognosis and/or diagnosis of osteoarthritis and/or subchondral bone sclerosis, as well as the method for determining or checking or diagnosis of the therapeutic effect of treatment of osteoarthritis and/or subchondral bone sclerosis in a mammalian individual, makes use of osteomodulin (OMD) protein or preferably fragment(s) of osteomodulin protein as a marker for the prognosis and/or diagnosis of osteoarthritis and/or subchondral bone sclerosis of mammals. These fragments are selected from the group consisting of a) to f).

a) osteomodulin fragment having N-terminal amino acid residue varying from amino acid position 21 to 148 and having C-terminal amino acid residue varying from amino acid position 162 to 235 in the amino acid sequence shown in SEQ ID NO: 1: b) osteomodulin fragment having N-terminal amino acid residue varying from amino acid position 224 to 261 and having C-terminal amino acid residue varying from amino acid position 276 to 421 in the amino acid sequence shown in SEQ ID NO: 1;

c) OMD-(131-223)
(OMD1 131-KIDYGVFAKLPNLLQLHLEHNNLEEFPFPLPKSLERLLL GYNEISKLQTNAMDGLVNLTMLDLCYNYLHDSLLKDKIFAKMEKLMQLN LCSNR-223 (SEQ ID NO: 2)), d) OMD-(236-296)
(OMD2 236-MYLSLENNSISSIPEKYFDKLPKLHTLRMSHNK LQDIPYN I FN LPN IVELSVGH N KLKQAF-296 (SEQ ID NO: 3)).

e) OMD-(148-162)
(OMD1 a 148-LEHNNLEEFPFPLPK-162 (SEQ ID NO: 4)), f) OMD-(261-276)
(OMD2a 261-LRMSHNKLQDIPYNI-276 (SEQ ID NO: 5)).

Quantification of serum OMD1, OMD2, OMD1 a and OMD2a, preferably OMD1 and OMD2, could also be used for the diagnostic of OA and the follow-up of anti-OA therapies. Further, as OA is a heterogeneous syndrome with different clinical phenotypes, osteomodulin fragments could be used in combination with other OA biomarkers to improve the knowledge of the patient disease and give information to do personalized medicine. In addition, OMD1, OMD2, OMD1 a and OMD2a, preferably OMD1 and OMD2, can also be used as a marker of sclerotic subchondral pre-osteoblasts and osteoblasts.

Although it is not yet clear if it precedes or occurs subsequently to cartilage damage, subchondral bone sclerosis is an important feature in OA pathophysiology. Subchondral bone sclerosis is characterized by local bone resorption and the accumulation of weakly mineralized osteoid substance. Subchondral bone sclerosis is suspected to be linked to cartilage degradation. not only in modifying the mechanical properties of the subchondral bone, but also by releasing biochemical factors with an activity on cartilage metabolism. The present inventors have previously demonstrated that osteoblasts isolated from subchondral OA bone expressed an altered phenotype. More precisely, it was demonstrated that osteoblasts coming from the thickening (called sclerotic, SC) of subchondral bone located just below a cartilage lesion exhibits an elevated alkaline phosphatase (AP) activity and express higher levels of IL-6, IL-8. PGE2, TGF-βI and type I collagen than osteoblasts coming from the non-thickening neighboring area (called non-sclerotic area. NSC). During the studies of the present invention this in vitro model was used to compare the secretome of NSC and SC osteoblasts.

DETAILED DESCRIPTION OF THE EMBODIMENTS OF THE PRESENT INVENTION

Definitions

Figure 1:
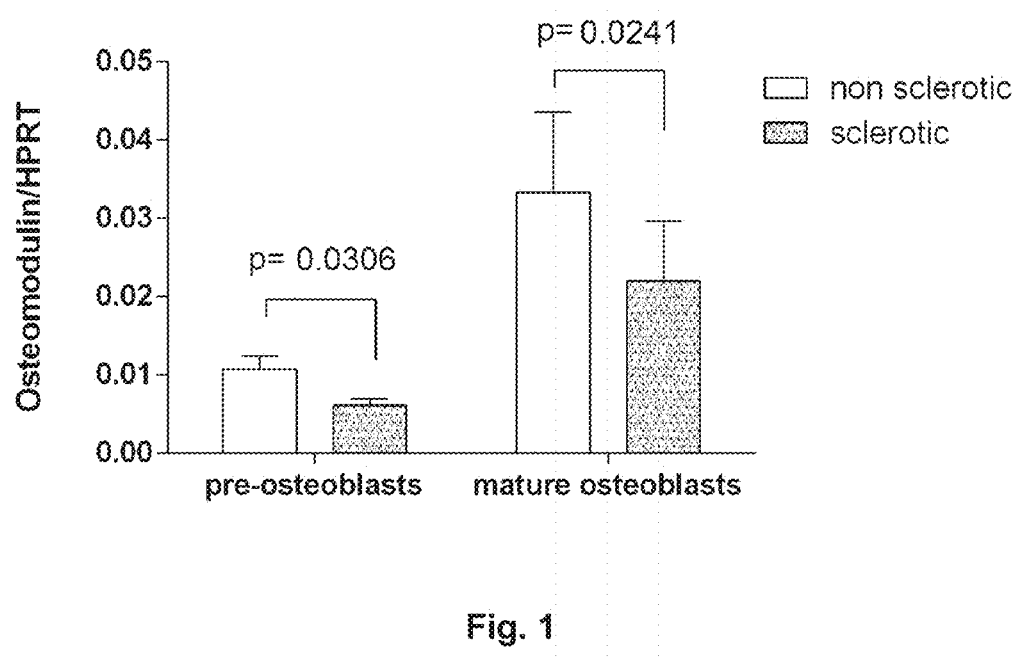
FIG. 1 shows osteomodulin gene expression by pre-osteoblasts or mature osteoblasts in non sclerotic or sclerotic cells. The mRNA copy numbers were normalized against the corresponding copy number of HPRT mRNA and results are the mean±SEM of five independent experiments performed with bone biopsy coming from different donors. In each experiment, each experimental condition was performed in duplicate. Comparison of mean values was performed by paired t-test. The results showed that osteomodulin is less expressed by sclerotic osteoblasts than non sclerotic osteoblasts.

As used herein "osteomodulin protein" or "OMD" refers to *Homo sapiens* osteomodulin represented by the amino acid sequence 1-421 of SEQ ID NO: 1. In preferred embodiments "osteomodulin protein" or "OMD". in particular "osteomodulin protein" or "OMD" for use in the prognosis and/or diagnosis of osteoarthritis and/or subchondral bone sclerosis. refers to the mature form of osteomodulin of *Homo sapiens* represented by the amino acid sequence 21-421 of SEQ ID NO: 1.

By "sample" is intended any biological sample obtained from an organism, in particular body fluids which contains, or is suspected to contain, a polypeptide or peptide selected from SEQ ID NOs: 1 to 5, preferably SEQ ID NOs: 2 to 5. As indicated, biological samples include body fluids which contain the polypeptides and/or peptides, and other tissue sources found to express the polypeptides and/or peptides. Methods for obtaining tissue biopsies and body fluids from organisms are well known in the art. Samples from the body fluids such as urine, secretions, interstitial fluid, blood, synovial fluid, serum, spinal fluid lymph. are particularly preferred and serum is most preferred.

The term "immunological binding partner" or "antibody" is used synonymously and is used in the broadest sense and specifically covers, for example, polyclonal antibodies. monoclonal antibodies, humanized antibodies. Fc fragments, Fab fragments, and antibody fragments that exhibit the desired biological or immunological activity, single chain antibodies (scFv), chimeric antibodies, biobetters or other antigen-specific antibody fragments specifically binding to polypeptides and peptide shown in SEQ ID NOs: 1 to 5, preferably SEQ ID NOs: 2 to 5. The term "immunoglobulin" (Ig) is used interchangeable with "antibody" herein.

The term "monoclonal antibody" as used herein refers to an antibody obtained from a population of substantially homogenous antibodies, i.e., the individual antibodies comprising the population are identical except for possibly naturally occurring mutations that may be present in minor amounts. Monoclonal antibodies are highly specific. being directed against a single antigenic site. Furthermore, in contrast to polyclonal antibody preparations which include different antibodies directed against different determinants (epitopes), each monoclonal antibody is directed against a single determinant on the antigen. In addition to their specificity. the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology or may be made using recombinant DNA methods in bacterial, eukaryotic animals or plant cells or may be isolated from phage antibody libraries.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such
antibodies, so long as they exhibit the desired biological activity. Chimeric antibodies of interest herein include "primatized" antibodies comprising variable domain antigen-binding sequences derived from a non-human primate (e.g. Old World Monkey. Ape etc), and human constant region sequences.

An "intact" antibody is one which comprises an antigen-binding site as well as a CL and at least heavy chain constant domains CH1, CH2 and CH3.

"Antibody fragments" comprise a portion of an intact antibody, preferably the antigen binding or variable region of the intact antibody. Examples of antibody fragments include Fab, Fab', F(ab')2, and Fv fragments; diabodies; linear antibodies; single-chain antibody molecules; and multispecific antibodies formed from antibody fragments.

Papain digestion of antibodies produces two identical antigen-binding fragments, called "Fab" fragments, and a residual "Fc" fragment. a designation reflecting the ability to crystallize readily. The Fab fragment consists of an entire L chain along with the variable region domain of the H chain (VH), and the first constant domain of one heavy chain (CH1). Each Fab fragment is monovalent with respect to antigen binding, i.e., it has a single antigen-binding site. Pepsin treatment of an antibody yields a single large F(ab')2 fragment which roughly corresponds to two disulfide linked Fab fragments having divalent antigen-binding activity and is still capable of cross-linking antigen. Fab' fragments differ from Fab fragments by having additional few residues at the carboxy terminus of the CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by
sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight. non-covalent association. From the folding of these two domains emanate six hypervariable loops (3 loops each from the H and L chain) that contribute the amino acid residues for antigen binding and confer antigen binding specificity to the antibody. However. even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably. the sFv polypeptide further comprises a polypeptide linker between the VH and VL domains which enables the sFv to form the desired structure for antigen binding.

The term "diabodies" refers to small antibody fragments prepared by constructing sFv fragments with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin.

An antibody or other organic molecule "which binds" an antigen of interest, e.g. a polypeptide or peptide selected from SEQ ID NOs: 1 to 5, preferably SEQ ID NOs: 2 to 5. is one that binds the antigen with sufficient affinity such that the antibody or other organic molecule is useful as a diagnostic agent in a cell, tissue and/or body fluid expressing the antigen, and does not significantly cross-react with other proteins. In such embodiments, the extent of binding of the antibody or other organic molecule to a "non-target" protein will be less than about 10% of the binding of the antibody or other organic molecule to its particular target protein as determined by radioimmunoprecipitation (RIA). With regard to the binding of an antibody or other organic molecule to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about $10^{-4}$ M. preferably at least about $10^{-5}$ M. preferably at least about $1^{-6}$ M, preferably at least about $10^{-7}$ M. preferably at least about $10^{-8}$ M,
preferably at least about $10^{-9}$ M, preferably at least about $10^{-10}$ M, preferably at least about $10^{-11}$ M. preferably at least about $10^{-12}$ M, or greater. In one embodiment, the term "specific binding" refers to binding where a molecule binds to a particular polypeptide or epitope on a particular polypeptide without substantially binding to any other polypeptide or polypeptide epitope.

The word "label" when used herein refers to a detectable compound or composition which is conjugated directly or indirectly to the antibody, oligopeptide or other organic molecule so as to generate a "labeled" antibody, oligopeptide or other organic molecule. The label may be detectable by itself (e.g. radioisotope labels or fluorescent labels) or, in the case of an enzymatic label, may catalyze chemical alteration of a substrate compound or composition which is detectable.

The terms "Western blot," "Western immunoblot" "immunoblot" and "Western" refer to the immunological analysis of protein(s), polypeptides or peptides that have been immobilized onto a membrane support. The proteins are first resolved by polyacrylamide gel electrophoresis (i.e., SDS-PAGE) to separate the proteins, followed by transfer of the protein from the gel to a solid support, such as nitrocellulose or a nylon membrane. The immobilized proteins are then exposed to an antibody having reactivity towards an antigen of interest. The binding of the antibody (i.e., the primary antibody) is detected by use of a secondary antibody which specifically binds the primary antibody. The secondary antibody is typically conjugated to an enzyme which permits visualization of the antigen-antibody complex by the production of a colored reaction product or catalyzes a luminescent enzymatic reaction (e.g., the ECL reagent, Amersham).

As used herein, the term "ELISA" refers to enzyme-linked immunosorbent assay (or EIA). Numerous ELISA methods and applications are known in the art, and are described in many references (See, e.g., Crowther, "Enzyme-Linked Immunosorbent Assay (ELISA)," in Molecular Biomethods Handbook. Rapley et al. [eds.], pp. 595-617, Humana Press, Inc., Totowa, N.J. [1998]; Harlow and Lane (eds.). Antibodies: A Laboratory Manual, Cold Spring Harbor Laboratory Press [1988]; Ausubel et al. (eds.), Current Protocols in Molecular Biology, Ch. 11, John Wiley & Sons, Inc., New York [1994]). In addition, there are numerous commercially available ELISA test systems.

One ELISA method is a "direct ELISA," where an antigen (e.g., a polypeptide or peptide selected from SEQ ID NOs: 1 to 5, preferably SEQ ID NOs: 2 to 5) in a sample is detected. In one embodiment of the direct ELISA, a sample containing antigen is exposed to a solid (i.e., stationary or immobilized) support (e.g., a microtiter plate well). The antigen within the sample becomes immobilized to the stationary phase, and is detected directly using an enzyme-conjugated antibody specific for the antigen.

In an alternative embodiment, an antibody specific for an antigen is detected in a sample. In this embodiment, a sample containing an antibody (e.g., an antibody specific for a polypeptide or peptide selected from SEQ ID NOs: 1 to 5, preferably SEQ ID NOs: 2 to 5, is immobilized to a solid support (e.g., a microtiter plate well). The antigen-specific antibody is subsequently detected using purified antigen and an enzyme-conjugated antibody specific for the antigen.

In another alternative embodiment, an "indirect ELISA" is used. In one embodiment, an antigen (or antibody) is immobilized to a solid support (e.g., a microtiter plate well) as in the direct ELISA, but is detected indirectly by first adding an antigen-specific antibody (or antigen), then followed by the addition of a detection antibody specific for the antibody that specifically binds the antigen, also known as "species-specific" antibodies (e.g., a goat anti-rabbit antibody), which are available from various manufacturers known to those in the art.

In other embodiments, a "sandwich ELISA" is used, where the antigen (e.g. contained in a test sample) is immobilized on a solid support (e.g., a microtiter plate) via an antibody (i.e., a capture antibody) that is immobilized on the solid support and is able to bind the antigen of interest. Following the affixing of a suitable capture antibody to the immobilized phase, a sample is then added to the microtiter plate well, followed by washing. If the antigen of interest is present in the sample, it is bound to the capture antibody present on the support. In some embodiments, a sandwich ELISA is a "direct sandwich" ELISA, where the captured antigen is detected directly by using an enzyme-conjugated antibody directed against the antigen. Alternatively, in other embodiments, a sandwich ELISA is an "indirect sandwich" ELISA, where the captured antigen is detected indirectly by using an antibody directed against the antigen, which is then detected by another enzyme-conjugated antibody which binds the antigen-specific antibody, thus forming an antibody-antigen-antibody-antibody complex. Suitable reporter reagents are then added to detect the third antibody. Alternatively, in some embodiments, any number of additional antibodies are added as necessary, in order to detect the antigen-antibody complex. In some preferred embodiments, these additional antibodies are labelled or tagged, so as to permit their visualization and/or quantitation.

As used herein, the term "capture antibody" refers to an antibody that is used in a sandwich ELISA to bind (i.e., capture) an antigen in a sample prior to detection of the antigen. For example, in some embodiments, a polyclonal antibody against a polypeptide or peptide selected from SEQ ID NOs: 1 to 5, preferably SEQ ID NOs: 2 to 5. serves as a capture antibody when immobilized in a microtiter plate well. This capture antibody binds the polypeptide and/or peptide present in a sample added to the well. In one embodiment of the present invention, biotinylated capture antibodies are used in the present invention in conjunction with avidin-coated solid support. Another antibody (i.e., the detection antibody) is then used to bind and detect the antigen-antibody complex, in effect forming a "sandwich" comprised of antibody-antigen-antibody (i.e., a sandwich ELISA).

As used herein, a "detection antibody" is an antibody which carries a means for visualization or quantitation. which is typically a conjugated enzyme moiety that typically yields a colored or fluorescent reaction product following the addition of a suitable substrate. Conjugated enzymes commonly used with detection antibodies in the ELISA include horseradish peroxidase, urease, alkaline phosphatase, glucoamylase and β-galactosidase. In some embodiments, the detection antibody is directed against the antigen of interest, while in other embodiments, the detection antibody is not directed against the antigen of interest. In some embodiments, the detection antibody is an anti-species antibody. Alternatively, the detection antibody is prepared with a label such as biotin, a fluorescent marker, or a radioisotope, and is detected and/or quantitated using this label.

As used herein, the terms "reporter reagent," "reporter molecule," "detection substrate" and "detection reagent" are used in reference to reagents which permit the detection and/or quantitation of an antibody bound to an antigen. For example, in some embodiments, the reporter reagent is a colorimetric substrate for an enzyme that has been conjugated to an antibody. Addition of a suitable substrate to the antibody-enzyme conjugate results in the production of a colorimetric or fluorimetric signal (e.g., following the binding of the conjugated antibody to the antigen of interest). Other reporter reagents include, but are not limited to, radioactive compounds. This definition also encompasses the use of biotin and avidin-based compounds (e.g., including but not limited to neutravidin and streptavidin) as part of the detection system.

As used herein, the term "signal" is used generally in reference to any detectable process that indicates that a reaction has occurred, for example, binding of antibody to antigen. It is contemplated that signals in the form of radioactivity, fluorimetric or colorimetric products/reagents will all find use with the present invention. In various embodiments of the present invention, the signal is assessed qualitatively, while in alternative embodiments, the signal is assessed quantitatively.

As used herein, the term "amplifier" is used in reference to a system which enhances the signal in a detection method, such as an ELISA (e.g., an alkaline phosphatase amplifier system used in an ELISA).

Methods of Detecting Polypeptides

Polypeptides or peptides of SEQ ID NOs: 1 to 5, preferably SEQ ID NOs: 2 to 5, can be detected, visualized, determined, quantitated, etc. according to any effective method. Useful methods include, but are not limited to, immunoassays, radioimmunoassay (RIA). ELISA, immunofluorescence, flow cytometry, histology, electron microscopy, light microscopy, in situ assays, immunoprecipitation, Western blot and the like.

Immunoassays may be carried out in liquid or on a support. For instance, a sample (e.g. blood, urine, tissue, body fluids, preferably serum) can be brought in contact with and immobilized onto a solid phase support or carrier such as nitrocellulose or other solid support capable of immobilizing cells, cell particles or soluble proteins. The support may then be washed with suitable buffers followed by treatment with detectably labeled antibody specifically recognizing a polypeptide or peptide of SEQ ID NOs: 1 to 5, preferably SEQ ID NOs: 2 to 5. The solid phase support can then be washed with a buffer a second time to remove unbound antibody. The amount of bound label on the solid support may then be detected by conventional means.

Diagnosis of a Bone and/or Cartilage Disorder, e.g. Osteoarthritis

The present invention also provides a method of prognosis and/or diagnosing a bone and/or cartilage disorder, such as osteoarthritis and/or subchondral bone sclerosis, in a mammal, which is based on the decreased expression and/or concentration of a polypeptide or peptide selected from SEQ ID NOs: 1 to 5, preferably SEQ ID NOs: 2 to 5, preferably to be measured in serum samples. The present invention provides a valuable clinical marker correlated with such a disorder.

Such methods comprise determining if a polypeptide or peptide selected from SEQ ID NOs: 1 to 5, preferably SEQ ID NOs: 2 to 5, is underexpressed in a test sample as compared to a normal sample. Polypeptides of SEQ ID NOs: 1 to 5, preferably SEQ ID NOs: 2 to 5, are selectively expressed in human bone as shown in the examples of this application. A decreased presence of a polypeptide or peptide selected from SEQ ID NOs: 1 to 5, preferably SEQ ID NOs: 2 to 5, in a patient-derived sample indicates osteoarthritis and/or subchondral bone sclerosis. The assay is carried out using any standard methodology that measures levels (as compared to known normal controls) of a certain protein, e.g., by Western blot assays or a quantitative assay such as ELISA. For example, a standard competitive ELISA format using an antibody specific for a polypeptide or peptide selected from SEQ ID NOs: 1 to 5, preferably SEQ ID NOs: 2 to 5, is used to quantify levels of the polypeptide. Alternatively, a sandwich ELISA using a first antibody as the capture antibody and a second antibody specific for a polypeptide or peptide selected from SEQ ID NOs: 1 to 5, preferably SEQ ID NOs: 2 to 5, as a detection antibody is used.

In one embodiment, the method comprises (a) obtaining a test sample from a patient suspected of having a bone and/or cartilage disorder (b) detecting an expression level of a polypeptide selected from the group consisting of SEQ ID NOs: 1 to 5, preferably SEQ ID NOs: 2 to 5, by assaying for a polypeptide selected from the group consisting of SEQ ID NOs: 1 to 5, preferably SEQ ID NOs: 2 to 5; and (c) comparing said level to that of a healthy control, whereby a decrease in the expression level of a polypeptide selected from the group consisting of SEQ ID NOs: 1 to 5, preferably SEQ ID NOs: 2 to 5 relative to the level of expression of a polypeptide selected from the group consisting of SEQ ID NOs: 1 to 5, preferably SEQ ID NOs: 2 to 5, in the control, indicates a positive result for a bone and/or a cartilage disorder such as osteoarthritis and/or subchondral bone sclerosis.

The present invention will be described in more detail by the following examples which shall not be understood as limiting in any way.

EXAMPLES

Example 1: Subchondral Osteoblasts Cell Culture

Tibial subchondral bone plates were obtained from 10 OA men undergoing knee replacement surgery. The age of the patients ranged from 42 to 83 years. After careful elimination of trabecular bone and articular cartilage, OA subchondral bone was dissected to separate non sclerotic (NSC) from SC zones. Only the subchondral bone zones with a thickness greater than 2 mm and either denuded or overlaid by fibrillated cartilage were considered as SC bone. Also, only the subchondral bone zones with a maximal thickness of 1 mm were considered as NSC bone. Osteoblasts from SC or NSC subchondral bone were then obtained by outgrowth from explants. At confluence, primary cells were collected by trypsinization, seeded (50.000 cells/cm2) in 12-well plates (12-well companion plates. Falcon, BD Biosciences) and grown for 3 days in DMEM containing 10% FBS, 100 U/ml penicillin, 100 g/ml streptomycin, 10 mM HEPES. At this stage they were considered as pre-osteoblasts (no alkaline phosphatase activity). Pre-osteoblasts were either used directly or differentiated in mature osteoblasts, by maintaining for further 14 days in a differentiation media, composed of DMEM containing 100 U/ml penicillin, 100 g/ml streptomycin, 10 mM HEPES, 2% Ultroser G, a serum substitute, $10^{-8}$ M 1,25-(OH)$_2$-vitamin D3 (Sigma-Aldrich, Belgium), 2 mM glutamine, 50 g/ml ascorbic acid and 20 g/ml proline. At the end of this differentiation period, cells expressed an osteoblast/osteocyte phenotype characterized by the production of osteocalcin and alkaline phosphatase, and were able to mineralize their matrix in presence of β-glycerophosphate.

For the experimentations, pre-osteoblasts or mature osteoblasts were rinsed and then cultured in a BSA/FBS free medium for 72 hours. The nutrient media used was DMEM supplemented with 1% ITS (Lonza, Belgium), 10 mM HEPES, 100 U/ml penicillin, 100 g/ml streptomycin, 2 mM glutamine (Lonza, Belgium), 50 g/ml ascorbic acid (Sigma-Aldrich. Belgium), 20 g/ml proline (Invitrogen, Belgium). ITS is a premixed cell growth system containing in one ml:

0.625 mg insulin, 0.625 mg transferrin, 0.625 g selenious acid. These conditioned 72 h supernatants were used to perform the secretome analysis.

Example 2: Proteomic Analysis

A proteomic analysis of osteoarthritic osteoblasts secretome was performed. using differential quantitative and relative label free analysis on nanoUPLC-Synapt HDMS G2 system (Waters). One patient was used to perform validation tests before 5 other patients with matched NSC and SC secretome were analyzed.

Protein Identification by LC-ESI-MS/MS

The samples were reduced, alkylated and reduced, concentrated using Amicon (Millipore) with membrane cut-off of 3 kDa. The protein content of the samples was then quantified using RCDC kit (Biorad). Aliquotes of 15 g for each sample were reduced, alkylated and reduced, concentrated using Amicon (Millipore) with membrane cut-off of 3 kDa, and then the 2D-Clean up kit (GE) was applied according to manufacturer recommendations, to eliminate impurities not compatible with mass spectrometry analysis. The protein pellets after the washing steps were further resolubilized in bicarbonate ammonium 50 mM. The samples were digested in solution with trypsin (16 hours at 37° C. ratio tryspin/total proteins (W7W) (1/50), 3 h at 37° C. with ratio 1/100 in 80% ACN). The reaction was stopped by addition of formic acid. The samples were evaporated to dryness in a speed vacuum. The samples were redissolved in water 0.1% formic acid then an aliquote corresponding to 3.5 g of protein digest for each sample was purified using a Zip-Tip C18 High Capacity according to manufacturer recommendations. The samples were evaporated to dryness in a speed vacuum.

The peptides were conditioned at 3.0 g in ammonium formiate 100 mM. with 150 fmoles in ADH per volume injected for the MPDS mix standard (Waters). The internal standards spiked at different ratio between sample spiked with MPDS mix 1 or 2 allows technical verification of the entire 2D-UPLC separation, MS-MSE data acquisition with additional ion mobility separation, PLGS identification process and also relative quantitative analysis. ADH being present at ratio MPDS1/MPDS2=1.

Differential quantitative and relative label free analysis on a nanoUPLC-Svnapt™ HDMS™ G2 system (Waters).

The principle of this method is to compare in a quantitative fashion, tryptic peptides digests of complex samples and spiked with different commercial internal standards which allows their relative quantification. The high sensitivity, resolution and mass accuracy of this mass spectrometer that combines high efficiency ion mobility (IMS) and Time of flight Mass Spectrometry (TOF-MS), together with the statistical software developed by Waters allows confident identification of the peptides and proteins present in the original peptides mixes to be compared.

The Synapt™ HDMS™ G2 mass spectrometer uses electropsray ionisation source (ESI) and allows sensitive detection (lower limit around 0.1 to 1 fmol of protein) with high resolution and high mass accuracy (within 10 ppm) for the analyzed peptides. All the peptides were fragmented (MSE) and their sequence and identity were be obtained after database searches and correlation to the accurate mass measured for each parent peptide fragmented.

Statistical analysis with ProteinLynx Global SERVER vs 2.5 included identification of the peptides and proteins and their relative quantification on the base of co-analysis of a second internal standard composed of several proteins digests, present in both samples to be compared at different abundance ratio. The linear dynamic range of this label free quantitative technique was around 3 to 4 order of magnitude.

PLGS Analysis

Protein identification was performed using the data base extracted from UNIPROT Sus Crofa with manual addition of the protein sequences used as spikes and internal standards: MPDS mix.

The PLGS score is a probabilistic score correlated to the degree of confidence regarding the identification of a protein. Therefore a high value of PLGS score correlates with the fact that a high quality and quantity of information was observed by MS and MSE. The score is attributed to the protein after database search. This database search involves also the search on a randomized database recomputed from the original data base to evaluate the risk of false positive protein identification. For identification, the minimum to consider is at least two different peptides per protein identified and to check the false positive rate, this should be as low as possible (the false positive rate will be of maximum 4% because of the settings used in PLGS database search).

The results show that osteomodulin is more abundant in non sclerotic secretome than in sclerotic secretome. As mentioned above, the proteomic analysis of osteoarthritic osteoblasts secretome was performed, using differential quantitative and relative label free analysis on nanoUPLC-Synapt HDMS G2 system (Waters) to discover the differential protein production between non sclerotic and sclerotic osteoblasts. With this proteomic analysis and using 6 patients, osteomodulin protein production was found to be 60% lower by sclerotic compared to non sclerotic osteoblasts in 4 patients ($p<0.001$), while undetectable in the 2 other patients in the sclerotic osteoblasts secretome.

In addition, different peptide fragments of osteomodulin were found in the proteomic study (fragments A-H) and matched with data from human body fluid, namely synovial fluid, urine, plasma). The fragments of osteomodulin and in which test samples they were found are summarized in the following table 1.

TABLE 1

Fragments of osteomodulin identified by proteomic analysis

| fragment | amino acid sequence relating to SEQ ID NO: 1 | source |
| --- | --- | --- |
| F, D and B | 131-176 | synovial fluid, urine, plasma |
| G | 214-223 | urine, plasma |
| E | 269-291 | urine, plasma |
| A | 300-314 | plasma |
| H | 342-366 | plasma |

Example 3: Expression of Osteomodulin in Osteoblasts. Measurement by Quantitative Real-Time RT PCR In order to show expression of osteomodulin in osteoblasts the mRNA levels of osteomodulin was analyzed in 5 patients. RNA from $1.10^6$ cells was isolated by RNeasy mini kit total RNA isolation system (Qiagen, Belgium) and polymerase chain reaction (PCR) was performed by using the Light Cycler-SYBR premix Ex Taq (Takara, Belgium). The PCR template source was either 3 ng first-strand cDNA or purified DNA standard. The following primer sequences were used to amplify the desired cDNA: HPRT forward 5'-TGTAATGACCAGTCAACAGGG-3' (SEQ ID NO: 6)

and reverse 5'-TGCCTGACCAAGGAAAGC-3' (SEQ ID NO: 7). Osteomodulin (OMD) forward 5'-TCCTGGTTTGCCTTICTTCACTT-3' (SEQ ID NO: 8) and reverse 5'-G G GTCAATAG AAG G ACACATCAC-3' (SEQ ID NO: 9). Hypoxanthine-guanine phosphoribosyl-transferase (HPRT) was used as an internal standard and the ratio of OMD to HPRT were calculated. Five patients were analyzed, and four of them are other ones than used in the proteomic analysis.

The results showed that osteomodulin is less expressed by sclerotic osteoblasts than non sclerotic osteoblasts. The mRNA levels of osteomodulin was analyzed in 5 patients. As result, a 0.57+/−0.19 fold between non sclerotic and sclerotic pre-osteoblasts (FIG. 1, p=0.0306) and 0.66+/−0.27 fold between non sclerotic and sclerotic mature osteoblasts (FIG. 1, p=−0.0241) was observed. In FIG. 1 osteomodulin gene expression by pre-osteoblasts or mature osteoblasts, in the non sclerotic or sclerotic cells is shown. The mRNA copy numbers were normalized against the corresponding copy number of HPRT mRNA and results are the mean±SEM of five independent experiments performed with bone biopsy coming from different donors. In each experiment, each experimental condition was performed in duplicate. Comparison of mean values was performed by paired t-test.

Example 4: Detection of the Presence of Osteomodulin and Osteomodulin Fragments in Human Serum by Western Blotting In order to assess this hypothesis that osteomodulin or osteomodulin fragments are present in the human serum and could be targeted as biomarker. human serum samples were analyzed by western blot using a goat polyclonal antiserum raised against the entire osteomodulin protein (R&D systems) in 3 healthy patients and osteoblasts culture supernatants.

Serum of 12 men were used in western-blotting experiments, 6 healthy and 6 suffering of severe OA. Before experiment serum were depleted in IgG and albumin using ProteoPrep kits (Sigma). During this process serum was diluted by approximately 3.3-fold. Subchondral osteoblast supernatants were 20-fold concentrated using Amicon Ultra 3 kDa 2 ml column (Millipore). Depleted serum (15 µl) or osteoblasts concentrated supernatant (6 µl=6 g total proteins) were fractioned by electrophoresis on a polyacrylamide gel (9%) and transferred onto a PVDF membrane. Membranes were blocked overnight 4° C. with Roche Blocking Reagent. Membranes were then incubated overnight at 4° C. with a biotinylated polyclonal goat antiserum, affinity purified, raised against the whole osteomodulin protein (BAF2884, R&D systems) 1:200 dilution in 0.5% Roche blocking reagent. Streptavidin-Horseradish peroxidase (HRP) (1:2500 dilution) was used as detection (Roche). The reaction was revealed with Luminata classico Western blotting substrate (Millipore) and capture with an ImageQuantl_AS4000 (Amersham).

Figure 2:
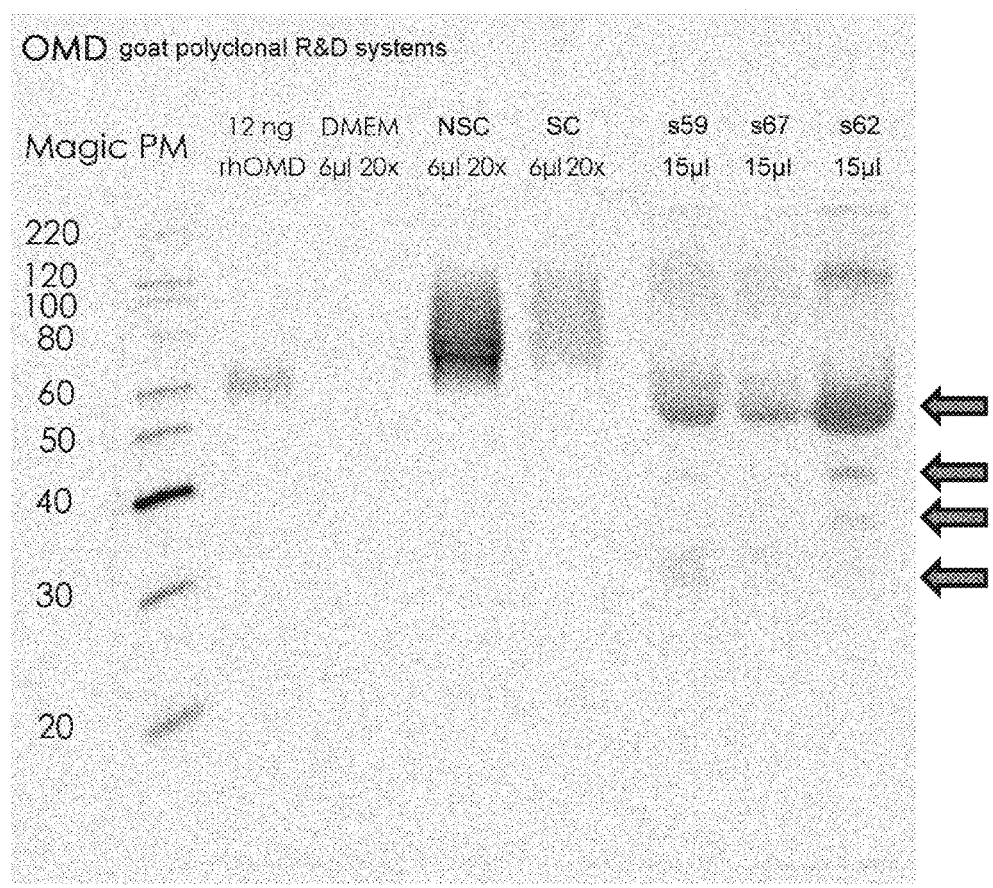
FIG. 2 shows a Western-blotting detection of osteomodulin using goat polyclonal antisera raised against entire osteomodulin. rhOMD: human recombinant osteomodulin (positive control), DMEM: concentration unconditioned culture supernatant (negative control), NSC: non sclerotic osteoblasts supernatant. SC: sclerotic osteoblasts supernatant, s59, s67, s62: serum of three healthy patients.

The results of the Western blotting for detecting the presence of osteomodulin and possible osteomodulin fragments in human serum are shown in FIG. 2 (lanes s59, s67. s62). In osteoblasts culture supernatants, the osteomodulin secreted appeared in two major bands at approximately 70 and 75 kDa, but with a variated pattern from 65 to 120 kDa probably due to a variation in glycosylation. The osteomodulin band was stronger in non sclerotic (NSC) than in sclerotic (SC) osteoblasts (FIG. 2. lanes NSC and SC). In human serum samples the major form of osteomodulin protein (detected about 54 kDa) was observed. Minor forms at about 42, 35 and 30 kDa (see arrows in FIG. 2) were also observed, which indicated that fragments of the protein were present in the circulating serum (FIG. 2. lanes s59, s67. s62).

In FIG. 2 the results of the Western-blotting detection of osteomodulin are shown, wherein the different lanes shown are as follows: rhOMD: human recombinant osteomodulin (positive control), DMEM: concentration unconditioned culture supernatant (negative control). NSC: non sclerotic osteoblasts supernatant, SC: sclerotic osteoblasts supernatant. s59, s67. s62: serum of three healthy patients.

Example 5: ELISA Development Targeting 2 Fragments of Osteomodulin

From the results obtained in Examples 2 and 4 and from datamining, the inventors assumed that the osteomodulin is cleaved in several peptides before these peptides arrive in the serum. In view of MMPs prediction cleavage sites. proteomics studies in biological fluid, and the fact that 70 residues C-terminal are considered to remain into the bone tissue, linked to the hydroxyapatite, two polypeptides were created and checked as potential biomarkers for osteoarthritis, OMD1 131-KIDYGVFAKLPNLLQLHLEHNN-LEEFPFPLPKSLERLLLGYNEISKLQTNAMDGLVNL TMLDLCYNYLHDSLLKDKIFAKMEKLMQLNLCSNR-223 (SEQ ID NO: 2) and OMD2 236-MYLSLENNSISSI-PEKYFDKLPKLHTLRMSHNKLQDIPYNIFNLPNIV-ELSVGHNK LKQAF-296 (SEQ ID NO: 3).

Preparing Antisera Directed to OMD1 and OMD2

To verify the hypothesis that osteomodulin fragments could be found in the serum and may serve as biomarker, BalbC mice were immunized against 2 peptides of osteomodulin, OMD1 a (148-LEHNNLEEFPFPLPK-162; SEQ ID NO: 4) and OMD2a (261-LRMSHNKLQDIPYNI-276; SEQ ID NO: 5)-KLH coupled peptides, respectively. The two different antisera obtained were specific to these sequences and did not show cross-reaction with 60% homolog peptides contained in the Lumican protein. Further, antiserum directed to OMD2 did not cross react with the sequence 268-290 of osteomodulin. Screening were made using biotinylated peptides, without the cysteine added for the KLH coupling, fixed on a streptavid in-coated 96-wells-plate. The competitive ELISA was carried using unbiotinylated and uncoupled peptide as competitor, with a standard curve concentrations comprise between 520 nM and 8 nM. Peroxidase AffiniPure Goat Anti-Mouse IgG, Fey Fragment Specific (Jackson ImmunoResearch) was used as secondary antibody (1:10000 dilution). Human sera dilution was shown to be parallel to the standard curve from 1:2 to 1:8 dilution in Diluent Reagent Buffer (D-Tek. Belgium). Assays were performed at 1:3 dilution of the sera for human and 1:5 for guinea pig. Culture supernatants were assayed undiluted.

Example 6: ELISA Using Human Serum for Detection of Osteomodulin Fragments

Figure 4:
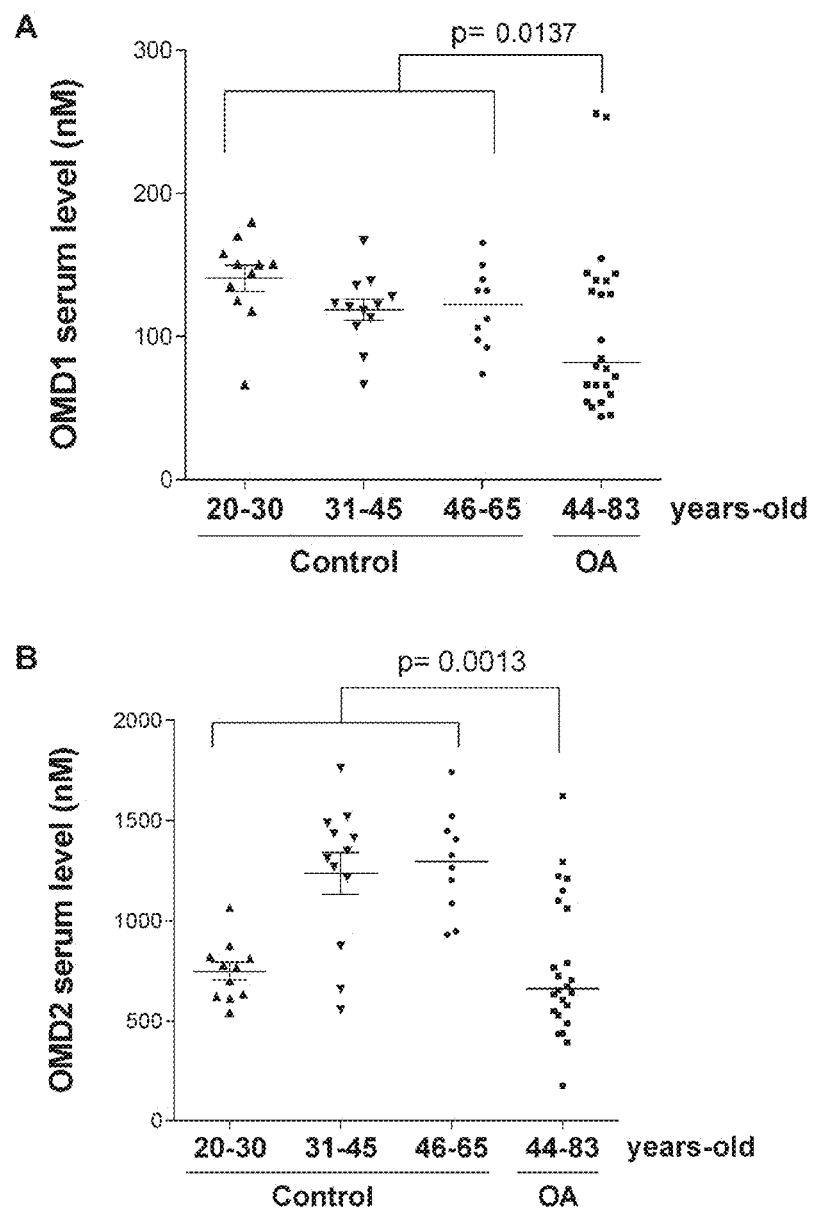
FIG. 4 consists of 4A and 4B and show the results of the analysis of levels of OMD1 and OMD2 in human serum. 33 healthy and 24 OA patients were quantified. In the healthy population, 11 were 20-30 years-old, 12 were 31-45-years-old and 10 were 46-65 years-old. The age range in OA population was 44-83 years. OMD1 and OMD2 were both significantly lower in OA compared to healthy patients.

The polyclonal antibodies directed to OMD1 and OMD2 prepared in Example 5 were used for detecting possible osteomodulin fragments in human serum by ELISA. In human serum, OMD1 and OMD2 in 33 healthy and 24 OA patients were quantified. In the healthy population, 11 were 20-30 years-old, 12 were 31-45-years-old and 10 were 46-65 years-old. The results are summarized in FIG. 4. The age range in OA population was 44-83 years. OMD1 and OMD2 were both significantly lower in OA compared to healthy patients (p=0.0137 and 0.0013, respectively, FIG. 4). The levels were not significantly different between men and women. The OMD1 level was not significantly different regarding age in healthy patient, but OMD2 level was lower in young 20-30 years-old patients compared to the 31-45 and 46-65-years-old groups.

Figure 3:
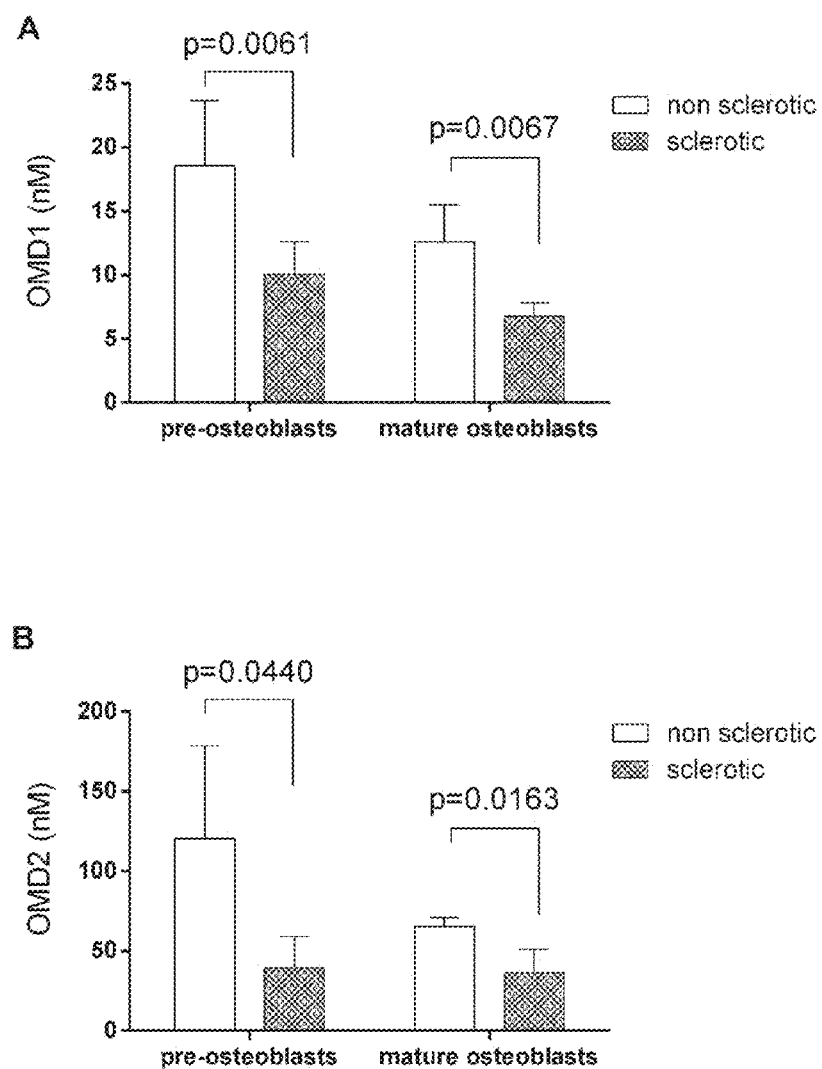
FIG. 3 consists of 3A and 3B and show the results of ELISA tests using antibodies against OMD1 and OMD2 peptide fragments. The figure shows the OMD1 and OMD2 concentration in non sclerotic or sclerotic pre-osteoblasts and osteoblasts culture supernatant. With this ELISA test fragments in osteoblasts culture supernatant were detected, and also the decrease of OMD1 and OMD2 in sclerotic secretome compared to non sclerotic secretome was confirmed.

Example 7: ELISA Using Osteoblasts Culture Supernatant for Detection of Osteomodulin Fragments Further an ELISA was carried out using the polyclonal antibodies directed to OMD1 and OMD2 prepared in Example 5 for detecting possible osteomodulin fragments in osteoblasts culture supernatant. In these ELISA tests fragments in osteoblasts culture supernatant were detected, and also the decrease of OMD1 and OMD2 in sclerotic secretome compared to non sclerotic secretome was confirmed. The results are summarized in FIG. 3. The figure shows OMD1 and OMD2 concentration in non sclerotic or sclerotic pre-osteoblasts and osteoblasts culture supernatant. Means+/−SD from 2 cultures of two independent experiments performed with bone biopsy coming from different donors. In each experiment, each experimental condition was performed in triplicate. Comparison of mean values was performed by paired t-test.

Example 8: Guinea Pig Spontaneous Model of OA

Figure 5:
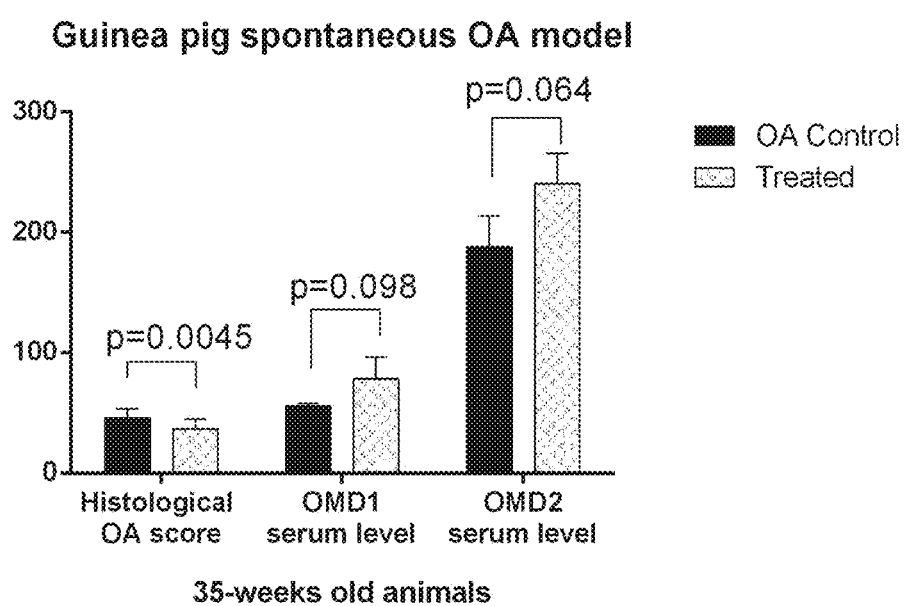
FIG. 5 shows the quantification of OMD1 and OMD2 in serum of a guinea pig spontaneous model of OA.

Further, OMD1 and OMD2 was assessed in a guinea pig spontaneous model of OA. In this model, guinea pig developed OA and at 35-week of age animals showed severe OA lesions quantifiable using the OARSI histological score. 15 animals were used in a control group and 15 animals were treated with a potential anti-OA treatment during 31 weeks. Beside a significant reduction in the histological OA score of the animals, an increase tendency of OMD1 and OMD2 levels in the serum was observed. The results are summarized in FIG. 5. The figure shows the quantification of OMD1 and OMD2 in OA guinea pig serum, in nM.

Example 9: Osteomodulin Mature Form [*Homo sapiens*] NP_005005.1

Figure 6:
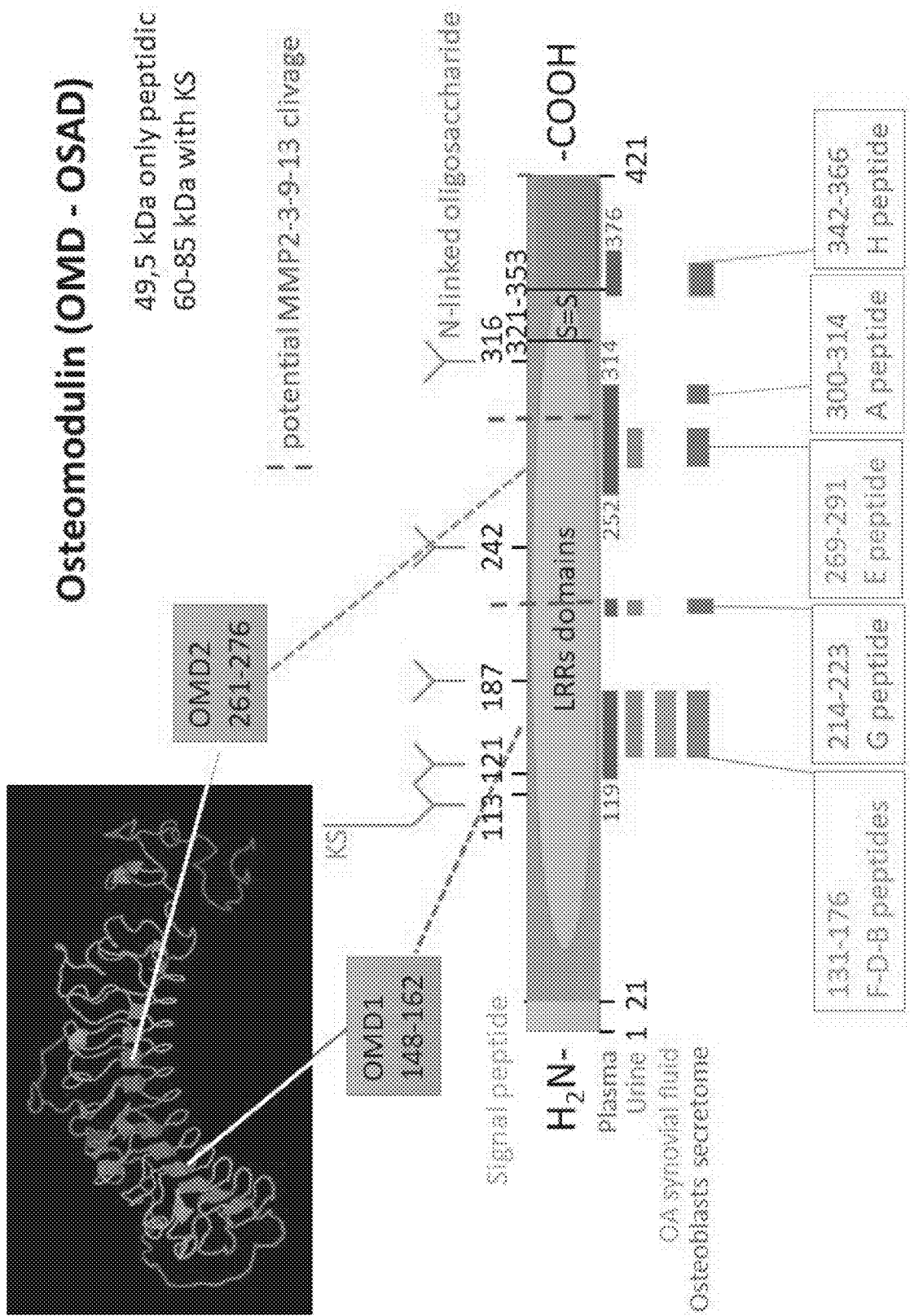
FIG. 6 shows detailed structure of Osteomodulin, wherein. LRRs: Leucin-Rich Repeats, S=S disulfide bond. KS: Keratan sulfate, MMP: matrix metalloproteinase. Different peptides found in our proteomic study are represented (A-H). and matched with data from human body fluid (synovial fluid, urine, plasma).

Osteomodulin mature form for *Homo sapiens* is represented by the amino acid positions 21-421 of SEQ ID NO: 1. The protein has a molecular weight of 49.5 kDa but depending to the glycosylation pattern it's estimated around 60 to 85 kDa (FIG. 6). We have schematized the general osteomodulin sequence, in regard to its crystallography structure, the predicted metalloproteinase clivage sites, and the different peptides found in mass spectrometry (FIG. 6).

In human serum, the inventors observed of the major form of osteomodulin protein (detected about 54 kDa). Minor form at about 42, 35 and 30 kDa are also observed, meaning that fragments of the protein could probably be present in the circulating serum.

According to this result and the structure of osteomodulin, the circulating fragments are larges and comprised at least half of the entire sequence. Considering the clivage prediction sites, and the mass spectrometry results in body fluid (FIG. 6), considering that some sequences are not find with mass spectrometry but it's due to the mass spectrometry technical limitation, the inventors reasonably conclude that the fragments recognized by the antibody directed against OMD1 and OMD2 are comprise as described in claim 4 or in any fragments comprising both OMD1 and OMD2 and representing more than half of the entire osteomodulin protein.

The invention claimed is:

1. Immunological binding partner specifically binding to an osteomodulin (OMD) protein fragment for use in the prognosis and/or diagnosis of osteoarthritis and/or subchondral bone sclerosis of mammals, wherein full-length osteomodulin protein is having the amino acid sequence shown in SEQ ID NO: 1, and wherein said fragment is selected from the group consisting c) to f):
 c) OMD-(131-223),
 d) OMD-(236-296),
 e) OMD-(148-162),
 f) OMD-(261-276).

2. Immunological binding partner specifically binding to an osteomodulin fragment, wherein full-length osteomodulin protein is having the amino acid sequence shown in SEQ ID NO: 1, and wherein said fragment is selected from the group consisting c) to f):
 c) OMD-(131-223),
 d) OMD-(236-296),
 e) OMD-(148-162),
 f) OMD-(261-276).

3. A kit comprising the immunological binding partner according to claim 1, wherein said immunological binding partner is selected from the group consisting of polyclonal antibodies, monoclonal antibodies, humanized antibodies, Fc fragments, Fab fragments, single chain antibodies (scFv), chimeric antibodies, biobetters and other antigen-specific antibody fragments.

4. A kit comprising the immunological binding partner according to claim 2, wherein said immunological binding partner is selected from the group consisting of polyclonal antibodies, monoclonal antibodies, humanized antibodies, Fc fragments, Fab fragments, single chain antibodies (scFv), chimeric antibodies, biobetters and other antigen-specific antibody fragments.

5. The immunological binding partner according to claim 1, wherein the mammals are human individuals.

* * * * *